(12) United States Patent
Ramanujam et al.

(10) Patent No.: US 7,570,988 B2
(45) Date of Patent: Aug. 4, 2009

(54) METHOD FOR EXTRACTION OF OPTICAL PROPERTIES FROM DIFFUSE REFLECTANCE SPECTRA

(75) Inventors: Nirmala Ramanujam, Janesville, WI (US); Gergory M. Palmer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 667 days.

(21) Appl. No.: 11/119,865

(22) Filed: May 2, 2005

(65) Prior Publication Data

US 2006/0247532 A1   Nov. 2, 2006

(51) Int. Cl.
*A61B 6/00* (2006.01)
(52) U.S. Cl. .................. 600/476; 702/19; 356/317; 356/303; 356/614
(58) Field of Classification Search ................ 600/476; 356/317, 303, 614, 244; 702/19
See application file for complete search history.

(56) References Cited

U.S. PATENT DOCUMENTS

2002/0084417 A1*  7/2002  Khalil et al. ............. 250/341.8

OTHER PUBLICATIONS

Bohnert et al., A Monte Carlo-based model for steady-state diffuse reflectance spectrometry in human skin: estimation of carbon monoxide concentration in livor mortis, Int J Legal Med (2005), 119:355-362. Published online: Apr. 21, 2005.*
Philippe Thueler et al, In Vivo Endoscopic Tissue Diagnostics Based On Spectroscopic Absorption, Scattering, And Phase Function Properties, Journal of Biomedical Optics, Jul. 2003, vol. 8 No. 3, pp. 495,503.

* cited by examiner

*Primary Examiner*—Eric F Winakur
*Assistant Examiner*—Katherine L Fernandez
(74) *Attorney, Agent, or Firm*—Quarles & Brady LLP

(57) ABSTRACT

An iterative process calculates the absorption and scattering coefficients of tissue from a set of diffuse reflectance measurements made with an optical spectrometer operating in the UV-VIS spectral range. The relationship between measured diffuse reflectance and the absorption and scattering coefficients is modeled using a Monte Carlo simulation.

18 Claims, 6 Drawing Sheets

METHOD FOR EXTRACTION OF OPTICAL PROPERTIES FROM DIFFUSE REFLECTANCE SPECTRA

STATEMENT REGARDING FEDERALLY SPONSORED RESEARCH

This invention was made with government support under Grant No. CA100559 and CA082710 awarded by the National Institute of Health. The United States Government has certain rights in this invention.

BACKGROUND OF THE INVENTION

The field of the invention is optical spectroscopy, and particularly, the measurement of optical properties of tissues with diffuse reflectance spectroscopy. Diffuse reflectance spectroscopy in the ultraviolet-visible (UV-VIS) wavelength range can be used to measure tissue absorption and scattering, which reflect the intrinsic physiological and structural properties of tissue, respectively. This technique has the potential to provide a real-time, non-destructive and quantitative means of characterizing tissue pathology. It thus presents an opportunity to fill a void in post-screening cancer care, where currently a biopsy is typically required to provide a definitive diagnosis. For example, in the case of breast cancer diagnosis, an image-guided needle biopsy procedure is commonly performed to determine whether a lesion is cancerous in women with a suspicious mammogram. However, such procedures are limited in that only a few small pieces of tissue can be removed. Additionally, the tissue must be fixed and read by a pathologist before a diagnosis can be made, often requiring a waiting period of several days to weeks. The limited sampling yield of breast needle biopsy results in a false-negative rate of 1-7% when verified with follow up mammography, as well as the requirement for repeat biopsies (percutaneous or surgical) in 9-18% of patients (due to discordance between histological findings and mammography).

Diffuse reflectance spectroscopy has the potential to improve the sampling accuracy of breast core needle biopsy. This technology can be deployed through fiber-optic probes to quickly and non-destructively identify the tissue type (normal, benign and malignant) at the needle tip during a breast biopsy procedure. A positive reading from the optical measurement will potentially increase the likelihood that a biopsy is being sampled from a tumor site. If the optical measurement reads negative, then the needle can be repositioned (along the needle track) to a new tissue site. Diffuse reflectance spectroscopy techniques can potentially make the breast biopsy procedure more accurate and less traumatic to the patient, while also reducing the number of biopsies that need to be processed in order to obtain a confirmatory diagnosis.

It is relatively straightforward to develop an instrument and fiber-optic probe for diffuse reflectance spectroscopy measurements in a clinical setting. However, the combined influence of absorption and scattering events upon diffusely reflected light in tissue make it difficult to interpret the physiological and structural content of the diffuse reflectance measurements, i.e. a change in measured diffuse reflectance can reflect a change in absorption, scattering, or both. Being able to separately quantify the independent absorption and scattering coefficients of tissue from a diffuse reflectance spectrum would enable the extraction of the physiological and structural properties of the sample, respectively. Knowledge of these sources of contrast can elucidate the underlying mechanisms that enable diagnosis and/or lead to an improvement in diagnostic algorithms.

Several analytical and numerical models have been developed to extract the absorption and scattering coefficients of tissue from fiber-optic based measurements of UV-VIS diffuse reflectance spectra. In general, these methods can be categorized into those using an analytical approximation of the transport equation (such as the diffusion equation), a modified form of the Monte Carlo model, and empirical methods. The diffusion equation is valid for the case where scattering is much greater than absorption and for relatively large photon travel paths, which is the case at near infrared (NIR) wavelengths. Monte Carlo modeling is a numerical technique that is valid for a wide range of absorption and scattering coefficients and photon paths and thus can be used to model light transport over the entire UV-VIS-NIR range. However, unlike the diffusion equation, the Monte Carlo technique is computationally intensive. These previously developed models are briefly discussed below.

A forward model of light transport based on the diffusion approximation is disclosed by Zonios et al "Diffuse reflectance spectroscopy of human adenomatous colon polyps in vivo," Appl Opt 38, 6628 (1999)". The diffuse reflectance spectra is expressed as a function of the wavelength-dependent reduced scattering coefficient and absorption coefficient, an empirically determined constant related to the probe geometry, and an empirically determined adjustment to the diffusion equation for use with high absorption coefficients. The empirical correction factors were determined using tissue phantom studies. The model was constrained to assume that hemoglobin is the only absorber that contributes to the wavelength dependent absorption coefficient, and the reduced scattering coefficient was constrained to be always decreasing with increasing wavelength. A non-linear least squares optimization routine was then employed to minimize the difference between the measured and fitted diffuse reflectance spectrum. The extracted reduced scattering coefficient was fit to Mie theory to extract scatterer size and scatterer density. This model was then used to extract the total hemoglobin concentration, scatterer size and scatterer density from diffuse reflectance spectra of colon tissues measured over the wavelength range of 350-700 nm. Both total hemoglobin concentration and scatterer size increased, while scatterer density decreased in adenomatous colon polyps compared to normal tissues.

The standard diffusion equation was improved by using a more complex model of light transport as described by Finlay et al, "Hemoglobin oxygen saturations in phantoms and in vivo from measurements of steady-state diffuse reflectance at a single, short source-detector separation," Med Phys 31, 1949 (2004). A $P_3$ approximation of the radiative transport equation was used, which incorporates higher order moments of anisotropy than the standard diffusion approximation. This modification performed better than the standard diffusion equation at short source-detector separations (>1 mm) and for relatively high absorption coefficients corresponding to those at UV-VIS wavelengths. Furthermore, this model was adaptable to complex fiber optic probe geometries. However, systematic deviations in the absorber concentration were observed at source-detector separations less than 1 mm, and for high absorber concentrations.

Another model disclosed by Ghosh et al "Measurement of optical transport properties of normal and malignant human breast tissue," Appl Opt 40, 176 (2001) is based on the standard diffusion approximation to extract the absorption and scattering coefficients from spatially resolved diffuse reflectance measurements, as opposed to spectrally resolved diffuse reflectance measurements. The spatially resolved diffuse reflectance is measured at 12 source-detector separations, ranging from 1.2 to 12 mm, over the wavelength range of 450-650 nm from human breast tissue samples. The absorption and scattering coefficients were determined from fits to the diffusion approximation of the spatially resolved diffuse reflectance at each individual wavelength. The results indicated that malignant tissues are more absorbing and scattering than normal tissues at all wavelengths.

A model based on Monte Carlo simulations is disclosed by Thueler et al "In vivo endoscopic tissue diagnostics based on spectroscopic absorption, scattering, and phase function properties," J Biomed Opt 8, 495 (2003), absorption and scattering coefficients are extracted from spatially resolved diffuse reflectance measurements. A scaling procedure is used to increase the efficiency of the Monte Carlo model. However, the scaling procedure is only valid for a low absorption coefficient range (corresponding to wavelengths greater than 500 nm). Spatially resolved diffuse reflectance measurements of esophageal tissues are made, using 10 source-detector separations ranging from 0.3 to 1.35 mm, over a wavelength range of 480-950 nm and fit the measurements at each wavelength to the Monte Carlo model. Results showed significant differences in the absorption and scattering coefficients of the normal antrum and fundus of the stomach.

An empirical method for the extraction of absorption and scattering coefficients from spatially resolved diffuse reflectance measurements is described by Pfefer et al "Reflectance-based determination of optical properties in highly attenuating tissue," J Biomed Opt 8, 206 (2003). A neural network is employed which was trained on phantoms, and then used this neural network model is used to extract optical properties from another set of phantoms. The spatially resolved diffuse reflectance is measured at six source-detector separations between 0.23 and 2.46 mm at a wavelength of 675 nm from phantoms with absorption coefficients ranging from 1-25 $cm^{-1}$ and reduced scattering coefficients ranging from 5-25 $cm^{-1}$. The neural network model is able to extract the absorption and scattering coefficients of the phantoms to within root mean square errors of $\pm 2$ $cm^{-1}$ and $\pm 3$ $cm^{-1}$, respectively.

A method for extracting the absorption and scattering coefficients from diffuse reflectance spectra of tissues and referred to as differential path-length spectroscopy is described by Amelink et al "In vivo measurement of the local optical properties of tissue by use of differential path-length spectroscopy," Opt Lett 29, 1087 (2004). By subtracting the reflectance measured from two adjacent fibers at a given wavelength, the resulting output (which was sensitive to a superficial portion of the tissue) can be expressed as a simple function of the absorption and scattering coefficients. Absorption and scattering coefficients are constrained in the model to be a function of the hemoglobin absorption and Mie scattering, respectively. This method is thus limited to a specific probe geometry. The diffuse reflectance spectra measured over a wavelength range of 350-1000 nm from normal and malignant bronchial mucosa is fit to this model. A statistically significant decrease in blood oxygenation in malignant tissue was found.

These prior methods demonstrate that extraction of optical properties (absorption and scattering coefficients) is feasible, and may be beneficial diagnostically. However, these prior methods are limited in that they place one or more of the following constraints on their applicability: they are limited to cases where absorption is lower than scattering, they impose constraints on the fiber-optic probe geometries used or require multiple illumination/collection fiber separations and/or they require extensive phantom studies for empirical calibration of the model. These limitations make these techniques difficult or impossible to implement on the large body of existing data that has been collected with a wide variety of probe geometries over the UV-VIS wavelength range.

SUMMARY OF THE INVENTION

The present invention is a method for extracting optical properties from tissue, which is based on Monte Carlo modeling of light transport and which is valid for a wide range of optical properties, including high absorption.

More particularly, the present invention is a method for calculating the scattering and absorption characteristics of tissue from diffuse reflectance measurements in an iterative process which repeatedly models reflectance values from a set of estimated tissue optical parameters using a Monte Carlo model and calculates the error between the measured diffuse reflectance and the modeled reflectance values; and calculating the scattering and absorption characteristics of the tissue from the estimated tissue optical parameters that result in a minimum error.

DETAILED DESCRIPTION OF THE PREFERRED EMBODIMENT

Figure 1:
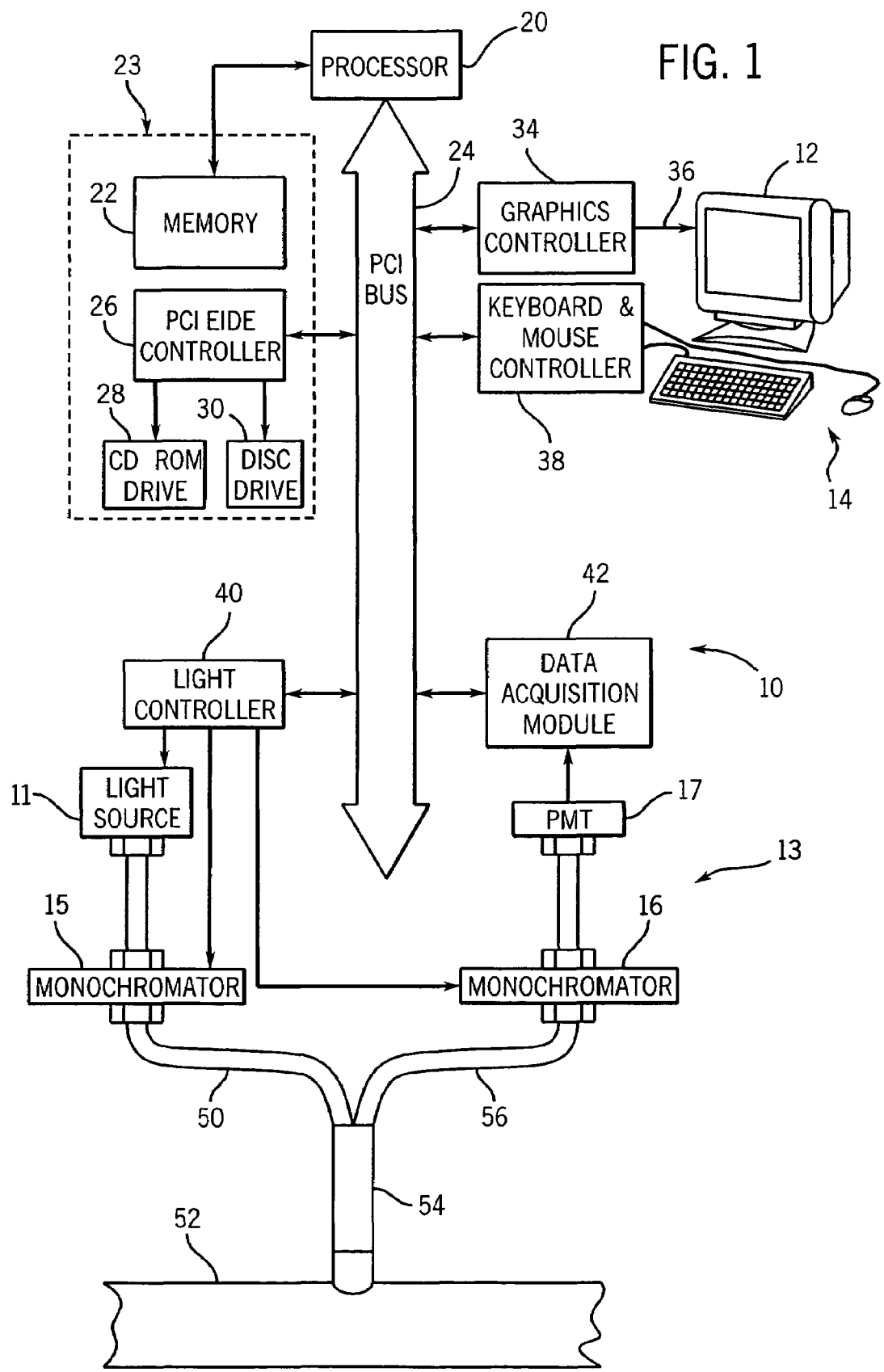
FIG. 1 is a pictorial representation of a spectrometer system which practices a preferred embodiment of the invention.

Referring particularly to FIG. 1, an optical spectroscopy instrument which employs the preferred embodiment of the invention includes a work station indicated generally at 10, which operates a light source 11 and receives optical data from a light detector indicated generally at 13. Under program control, the workstation 10 controls the light source 11 and detector 13 to carry out a prescribed optical spectroscopy measurement and to process the acquired optical data according to the present application as described in detail below.

The computer workstation 10 includes a processor 20 which executes program instructions stored in a memory 22 that forms part of a storage system 23. The processor 20 is a commercially available device designed to operate with one of the Microsoft Corporation Windows operating systems. In includes internal memory and I/O control to facilitate system integration and integral memory management circuitry for handling all external memory 22. The processor 20 also includes a PCI bus driver which provides a direct interface with a 32-bit PCI bus 24.

The PCI bus 24 is an industry standard bus that transfers 32-bits of data between the processor 20 and a number of peripheral controller cards. These include a PCI EIDE controller 26 which provides a high-speed transfer of data to and from a CD ROM drive 28 and a disc drive 30. A graphics controller 34 couples the PCI bus 24 to a CRT monitor 12 through a standard VGA connection 36, and a keyboard and mouse controller 38 receives data that is manually input through a keyboard and mouse 14.

The PCI bus 24 also connects to a light controller 40. The light controller 40 operates a light source 11, a source monochromator 15, and a detector monochromator 16 under program control. A data acquisition module 42 also connects to the PCI bus 24 to receive and input optical data received from a photomultiplier tube (PMT) 17.

The workstation 10 operates under program control to produce monochromatic light in an illumination fiber 50 that is applied to the subject 52 of the measurement by a probe 54. In the preferred embodiment the subject 52 is tissue and a probe 54 such as that disclosed in copending U.S. patent application Ser. No. 10/986,605 filed on Nov. 12, 2004 and entitled "Depth-Resolved Fluorescence Instrument With Angled Excitation" is preferred although many other commercially available probes may also be used. The light is projected into the subject 52 where it is absorbed, skattered and reflected as a function of the optical characteristics of the subject 52 and the wavelength of the light. The distal end of a detector optical fiber 56 is also disposed in the probe 54, and it collects light emanating from the subject 52 and couples it to the detector monochromator 16.

The above instrument is utilized to measure the diffusely reflected light over a range of wavelengths, spanning the UV-VIS spectrum (the wavelength range of measurement in the study described herein is 300-700 nm). There are two commonly used methods of obtaining such a measurement. The first uses a single channel detector, such as the photomultiplier tube (PMT) 17. In this preferred embodiment, the illumination and collection monochromators 15 and 16 are synchronously scanned over the wavelength range of measurement, and signal intensity is measured by the PMT 17 at specified wavelength increments over the wavelength range. In this way, the diffuse reflectance is recorded as a function of wavelength. In a second embodiment a multichannel array of detectors, such as that present in a charge coupled device (CCD) is employed in place of the PMT 17. In this case white light is delivered to the subject, and the collected light is coupled to a dispersive element, such as a diffraction grating. Different wavelengths of light are then directed towards separate detectors in the CCD array, and in this way, the diffuse reflectance over a wide range of wavelengths is acquired simultaneously.

The present invention is a method for processing the acquired optical data that measures the diffuse reflectance of the subject 52 to produce optical properties of the subject 52 such as its scattering coefficient $\mu_s$ and the absorption coefficient $\mu_a$ at different light wavelengths $\lambda$. This processing is based on a Monte Carlo model which relates the diffuse reflectance measurements to the desired optical properties.

Figure 2:
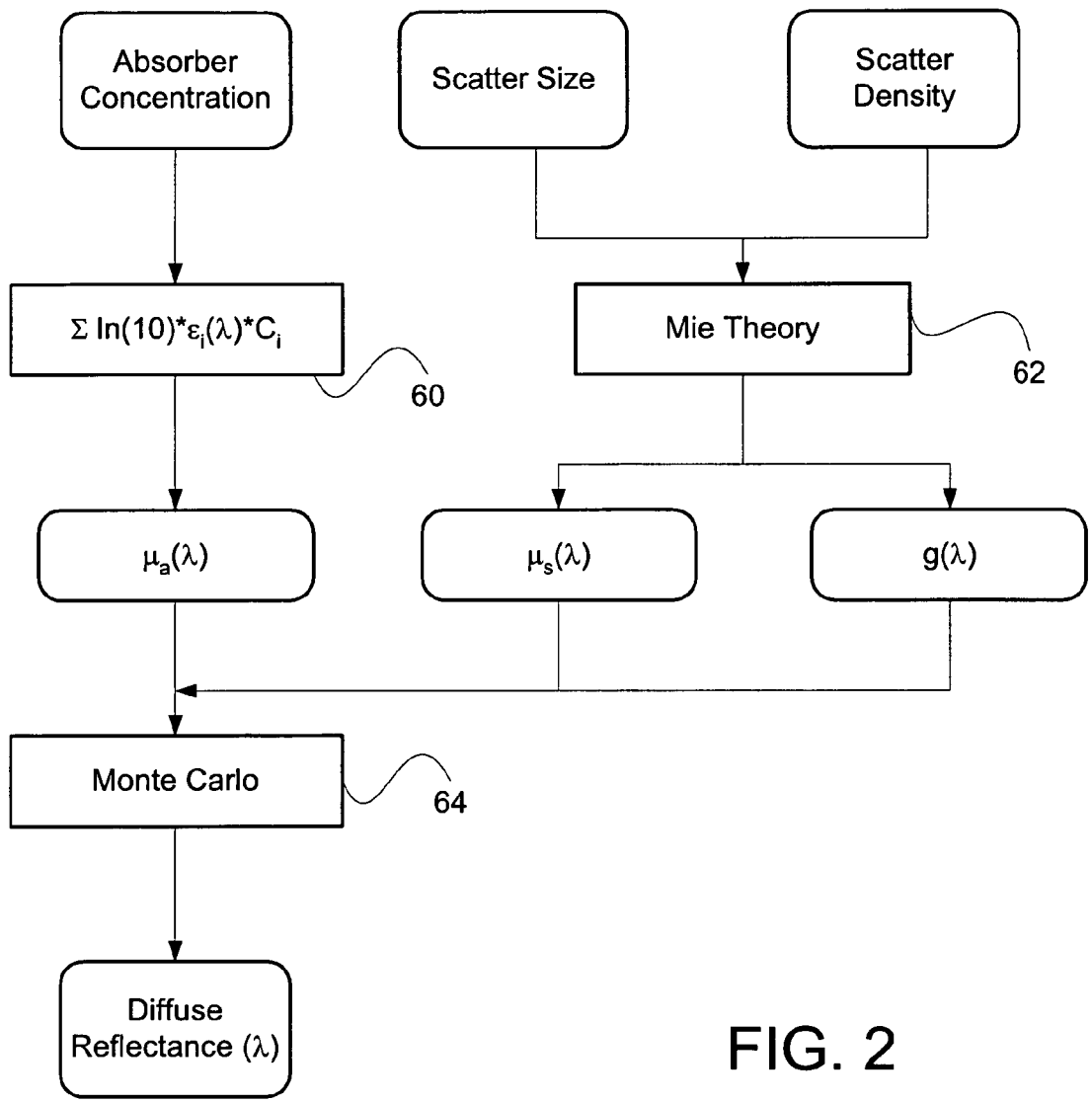
FIG. 2 is a block diagram of a Monte Carlo-based modeling method used in the system of FIG. 1.

The forward model refers to the model that relates the physiological and structural properties of the tissue to its measured diffuse reflectance. Referring to FIG. 2, the model employed with the present invention has two sets of inputs, which are used to determine the absorption and scattering coefficients, respectively. Beer's law indicated at 60 is used to model absorption. The concentration ($C_i$) of each chromophore (a free optical parameter) and the corresponding wavelength dependent extinction coefficient ($\epsilon_i(\lambda)$) (a fixed optical parameter) are used to determine the wavelength dependent absorption coefficient ($\mu_a(\lambda)$), according to the relationship given by Beer's law, $\mu_a(\lambda)=\Sigma\ln(10)\epsilon_i(\lambda)C_i$. The Mie theory for spherical particles described by C. F. Bohren et al *Absorption and scattering of light by small particles*. 1983, New York: Wiley. xiv is used to model scattering as indicated at 62. The scatterer size and density (free optical parameters) and the refractive index being fixed according to known values for phantoms, and expected values for tissue (see below) are used to determine the scattering coefficient ($\mu_s(\lambda)$) and the anisotropy factor ($g(\lambda)$) at a given wavelength.

The calculated optical properties (($\mu_a(\lambda)$, $\mu_s(\lambda)$ and $g(\lambda)$) of the tissue can then be input into a Monte Carlo model of light transport to obtain the "modeled" diffuse reflectance for a given wavelength. The software used for this purpose was adapted from that described by Wang et al. "MCML—Monte Carlo modeling of light transport in multi-layered tissues," Comput Methods Programs Biomed 47, 131 (1995). Note that a Monte Carlo simulation would be required for each unique set of optical properties, thus making this step of the forward model computationally prohibitive. To increase the efficiency of this step it is a teaching of the present invention that a scaling approach such as that described by Graaff et al. "Condensed Monte Carlo simulations for the description of light transport [biological tissue]," Appl Opt 32, 426 (1993) may be employed so that a single Monte Carlo simulation can be run and the output can be scaled to any set of optical properties. The method consists of running a single simulation for a given set of absorption ($\mu_{a,sim}$) and scattering coefficients ($\mu_{s,sim}$), and recording the exit weight ($W_{exit,sim}$), net distance traveled ($r_{t,sim}$), and total number of interactions for each photon (N) that exits the tissue surface. The scaling method then uses these stored parameters to calculate the new exit weight ($W_{exit,new}$) according to Equation (1) and the net distance traveled ($r_{t,new}$) according to Equation (2) for a given photon in the same simulation, but with new tissue absorption ($\mu_{a,new}$) and scattering coefficients ($\mu_{s,new}$). The scaling relationships, taken from Graaff et al., are given below.

$$W_{exit,new} = W_{exit,sim}\left(\frac{\mu_{s,new}}{\mu_{s,new} + \mu_{a,new}} * \frac{\mu_{s,sim} + \mu_{a,sim}}{\mu_{s,sim}}\right)^N \quad (1)$$

$$r_{t,new} = r_{t,sim}\left(\frac{\mu_{s,sim} + \mu_{a,sim}}{\mu_{s,new} + \mu_{a,new}}\right) \quad (2)$$

To further simplify the scaling process, it is assumed that for a given value of the reduced scattering coefficient, $\mu_s'=\mu_s\times(1-g)$, the diffuse reflectance is the same for any value of $\mu_s$ and $g$ that generate the same $\mu_s'$. This has been shown to be valid over the range of g values present in human tissue, i.e., for g values greater than 0.8. Using this similarity relation, and the scaling procedure outlined above, only a single Monte Carlo simulation needs to be run to determine the output diffuse reflectance of a Monte Carlo simulation for any set of optical properties.

The Henyey-Greenstein phase function is used in the single Monte Carlo simulation. The parameters of the single Monte Carlo simulation are as follows: number of photons: 40 million; $\mu_s$: 150 cm$^{-1}$; $\mu_a$: 0 cm$^{-1}$; g: 0.8; model dimensions: 2 cm (radius)×2 cm (depth); refractive indices: 1.33 (medium for phantoms); 1.36 (medium for tissue); and 1.452 (fiber-optic probe above medium in both cases).

A method of convolution is used to integrate over the illumination and collection fibers in order to determine the probability that a photon, traveling a fixed distance, would be collected for a given probe geometry. This takes advantage of the spatial and rotational invariance present in a homogeneous medium. For a pair of illumination and collection fibers, the probability of collection of a photon with a distance $r_t$ between the points of entering and leaving is given by:

$$\frac{1}{\pi^2 r_i^2} \int_{max(-r_i, s-r_t-r_c)}^{min(r_i, s-r_t+r_c)} (s-x) \cos^{-1}\left(\frac{s^2 + (s-x)^2 - r_i^2}{2(s-x)s}\right) \cos^{-1}\left(\frac{r_t^2 + (s-x)^2 - r_c^2}{2(s-x)r_t}\right) dx \quad (3)$$

where $r_i$ is the radius of the illumination fiber, $r_c$ is the radius of the collection fiber, s is the separation between the centers of the illumination and collection fibers, and x is the spatial variable over which the integral is taken. See Appendix A for the derivation of this formula. This equation is numerically integrated. To adapt this for the fiber bundle in the probe 54, the common end of the fiber bundle is imaged, and the centers of each illumination and collection fiber in the bundle is determined. Then the probe geometry is integrated pair-wise (for each illumination-collection fiber pair) to determine the total probability of collection. It was found that imaging the fiber bundle to obtain the exact location of each illumination and collection fiber was necessary to reduce errors caused by imperfect physical placement of the fibers within the probe bundle 54.

It was found that the scaling process and subsequent numerical integration for the probe geometry of a large number of photons required approximately 1 second to complete, which, while much faster than running an independent simulation, was still rather slow for performing an inversion procedure. Therefore, the diffuse reflectance values for a range of optical properties ($\mu_s$: 5-500 cm$^{-1}$, $\mu_a$: 0-200 cm$^{-1}$, g: 0.8) was determined ahead of time to form a lookup table, and cubic splines are used to interpolate between these table values. The smallest increment used in the lookup table was 0.1 cm$^{-1}$ for $\mu_a$, and 2.5 cm$^{-1}$ for $\mu_s$.

This forward, Monte Carlo-based model that relates reflectance values (Refl ($\lambda$)) to tissue optical properties is employed in an iterative process to calculate tissue optical properties from measured reflectance values Refl $(\lambda)_{meas}$. This iterative process is performed in the workstation 10 under the direction of a program stored in memory 23. Prior to processing tissue measurements the system is calibrated using a reference phantom, having known optical properties. The diffuse reflectance of the phantom is measured using the same procedures as for the tissue measurements. In addition, the modeled diffuse reflectance is calculated using the Monte Carlo model, based on the known optical properties of the phantom. Then the measured diffuse reflectance spectrum subsequently acquired from tissue is normalized to that obtained from the phantom. Similarly the modeled diffuse reflectance spectrum is normalized to the modeled diffuse reflectance spectrum from the phantom. This corrects for the system response, and differences in magnitude between the measured and modeled spectra present since the Monte Carlo model is on an absolute intensity scale, while the experimentally measured spectra is typically measured relative to a calibration standard.

Figure 3:
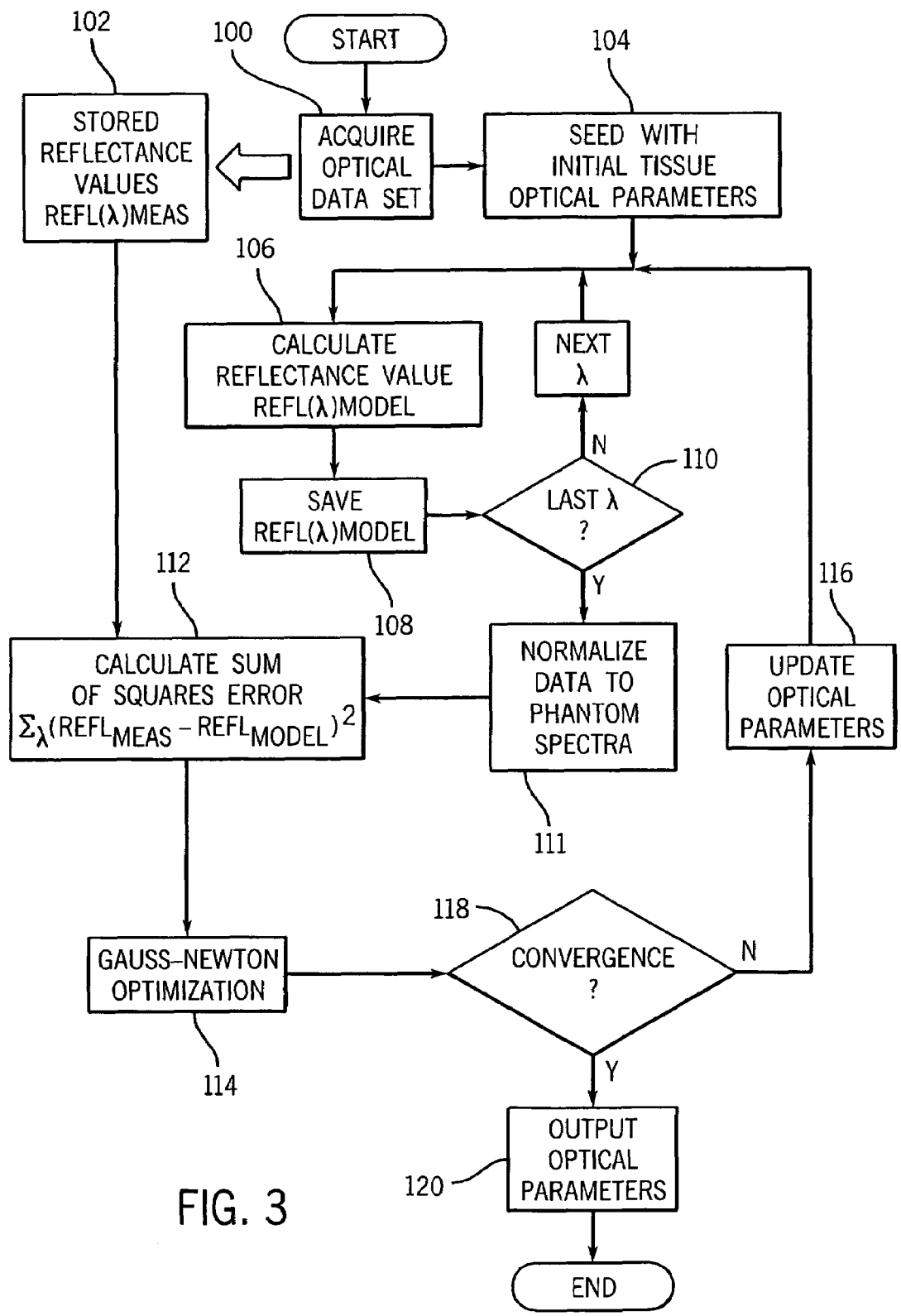
FIG. 3 is a flow chart of a preferred embodiment of the method of the present invention that employs the modeling method of FIG. 2 in the system of FIG. 1.

Referring particularly to FIG. 3, the first step of the method is to acquire an optical data set as indicated at process block 100 using the optical spectrometer instrument. This results in a set of measured reflectance values Refl $(\lambda)_{meas}$ taken at the set of specific light wavelengths ($\lambda$). This data is normalized to the diffuse reflectance spectrum obtained with the known phantom to calibrate for system/wavelength response and is stored in memory as indicated at 102.

Such measurements may be made in a number of different ways. In one method measurements are made by placing the probe in contact with a tissue sample soon after it has been biopsied during breast cancer or breast reduction surgery. These measurements may also be used for assessing margins during breast cancer surgery, by placing a probe in contact with the tumor bed after it has been removed from the patient. This allows for diagnosis of the remaining tissue left in the patient, and such a diagnosis allows the surgeon to determine whether more tissue needs to be removed. In the alternative, a fiber optic probe such as that described in co-pending U.S. patent application Ser. No. 11/063,273 filed on Feb. 22, 2005 and entitled "Side-Firing Optical Probe For Core Needle Biopsy", may be inserted into a hollow bore needle, such as those used during fine needle aspiration and core needle biopsy procedures. This technique allows for a near real time diagnosis, and assists in the correct positioning of the needle and/or eliminates the need for removal of tissue during these procedures.

As indicated at process block 104, the next step is to input a best estimate of tissue optical properties. These values will depend, of course, on the tissues being measured and the particular instrument being used. The optical parameters include "free" parameters such as absorber concentration, scatterer size and scatterer density. Optical parameters also includes "fixed" parameters such as excitation coefficient of the absorber and the refractive index of the scatterer and surrounding medium for each measurement wavelength ($\lambda$). For each measurement wavelength ($\lambda$) a reflectance value Refl $(\lambda)_{model}$ is calculated and stored at process block 108. When the value for the last wavelength ($\lambda$) is calculated as determined at decision block 110, the modeled reflectance values are normalized to the phantom diffuse reflectance spectrum to calibrate for system/wavelength response as indicated at process block 111. A calculation of the sum of squares error is then performed at process block 112. This measures the difference between the measured reflectance values Refl $(\lambda)_{meas}$ for the subject tissue and the corresponding values Refl $(\lambda)_{model}$ predicted by the forward model and then sums the squares of these differences. A Gauss-Newton nonlinear least squares optimization algorithm indicated at process block 114 is employed. This process is in the Matlab optimization toolbox available commercially from the Mathworks, Inc. of Natick Mass. and is used to minimize the error over the course of the iteration process. The free optical parameters are updated at process block 116 and the system loops back to repeat the process and measure the error produced using the newly updated optical parameters. When the trial optical parameters converge with the tissue optical parameters to produce a minimum error at process block 112, the process ends as indicated at decision block 118. The optical parameters $\mu_a(\lambda)$ and $\mu_s(\lambda)$ produced by the forward model using the final trial optical parameters are output as indicated at process block 120. In addition the free optical parameters absorber concentration, scatter size and scatter density my also be output and used for diagnostic purposes. To ensure convergence to a global minimum error, the above procedure may be repeated several times using different sets of initial tissue optical parameters at process block 104.

The inverse Monte Carlo model was used to extract optical properties from diffuse reflectance spectra collected from 41 human breast tissues taken from 23 patients undergoing breast cancer or breast reduction surgery. There were a total of 17 malignant tissue samples, 6 normal and 4 benign fibrous/glandular tissues, and 14 adipose tissues, as determined by the gold standard, histopathology. These spectra were collected in a previous study, and a detailed description of the methodology employed is provided in Palmer et al. "Comparison of multiexcitation fluorescence and diffuse reflectance spectroscopy for the diagnosis of breast cancer," IEEE Trans Biomed Eng 50, 1233 (2003).

The measured diffuse reflectance spectra of breast tissues were fit to the inverse model using the preferred method described above. In this case, one phantom was used as the reference phantom to calibrate the tissue diffuse reflectance spectra before the fitting procedure was carried out. This phantom contains a hemoglobin absorber H0267, commercially available from Sigma Company of St. Louis, Mo. and a scatterer of 1 μm diameter polystyrene spheres 07310-15, commercially available from Polysciences, Inc. of Warrington, Pa. It has a mean $\mu_s$ of 13.3 cm$^{-1}$ over a range of 10.9-16.4 cm$^{-1}$ and a mean $\mu_a$ of 0.9 cm$^{-1}$ over a range of 0.02 to 7.7 cm$^{-1}$. Mie theory was used to calculate the phantom's scattering properties, and a spectrophotometer was used to establish the absorption properties of the phantom. The diffuse reflectance of the phantom is measured using the same procedures as for the tissue measurements. In addition, the modeled diffuse reflectance is calculated using the Monte Carlo model, based on the known optical properties of the phantom. Then the measured diffuse reflectance spectrum from the tissue sample is normalized at each wavelength to that obtained from the phantom. Similarly the modeled diffuse reflectance spectrum is normalized to the modeled diffuse reflectance spectrum from the phantom. This corrects for the wavelength dependent system response, including the difference in magnitude between the measured and modeled spectra present since the Monte Carlo model is on an absolute intensity scale, while the experimentally measured spectra is measured relative to a calibration standard.

In tissue, the indices of refraction are fixed optical parameters and are assumed to be 1.4 and 1.36, respectively, for the scatterers and surrounding medium. The free optical parameters are the scatterer size and density. The scatterer size was constrained to be between 0.35 and 1.5μ diameter. The intrinsic chromophores were assumed to be oxygenated and deoxygenated hemoglobin, and β-carotene, and their wavelength dependent extinction coefficients were obtained from an online database. Lymphazurin (Cat# 00592358, Tyco Healthcare, Mansfield, Mass.), a dye used to locate the sentinel lymph node during surgery, was also included as an absorber since it was found to be present in some of the tissue samples. Its wavelength dependent extinction coefficient was measured using an absorption spectrophotometer. The free parameters of the fit for absorption were the concentrations of each of these absorbers.

Figure 4:
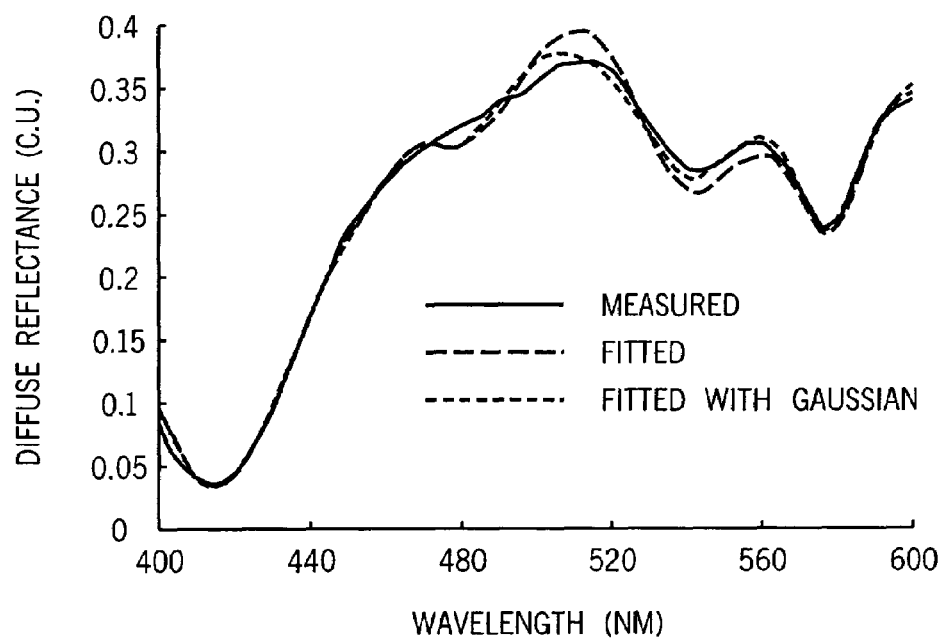
FIG. 4 is a graph of measured and modeled reflectance values as a function of light wavelength ($\lambda$) on malignant breast tissue.
Figure 5:
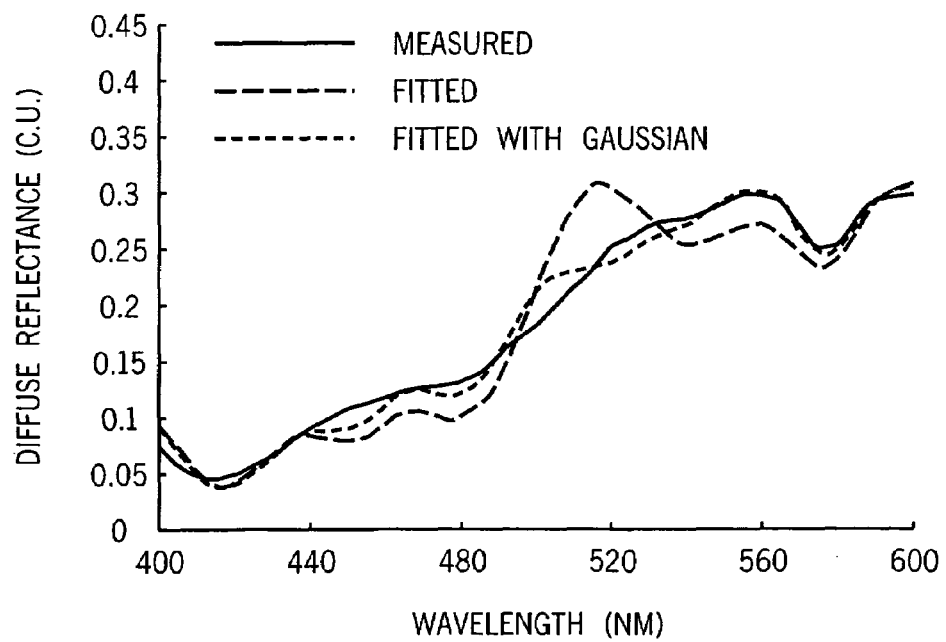
FIG. 5 is a graph of measured and modeled reflectance values as a function of wavelength of adipose breast tissue.

FIG. 4 shows measured diffuse reflectance spectra of a malignant tissue and FIG. 5 shows an adipose breast tissue sample, obtained from the same patient. The corresponding modeled spectra using the inverse Monte Carlo model in two different ways is also shown. The first modeled fit included the four absorbers, oxygenated hemoglobin, deoxygenated hemoglobin, β-carotene and lymphazurin and the second modeled fit included the four absorbers and an additional Gaussian function (fitted with Gaussian). It should be pointed out that when only the four absorbers are used in the fit (fitted), a deviation from the measured spectra is present at around 500-530 nm. This deviation was present in fits to the diffuse reflectance spectra of a number of tissue samples and likely indicates a region where the absorbers present in the tissue are not well described by the inverse model. To further evaluate this possibility, a Gaussian function was included as an additional absorbing component in the fit to the inverse model (fitted with Gaussian). The mean of the function was fixed at 515 nm, while the standard deviation of the function and contribution of the function to the fit were set as free parameters. It can be seen that the addition of this Gaussian function substantially improves the quality of the fits. Furthermore, for the majority of the fits (33 out of 41), the Gaussian function was found to have a standard deviation between 9 and 16 nm, with an average value of 13 nm. Repeating the fits to the inverse model with a Gaussian function with a mean of 515 nm and a standard deviation of 13 nm produced a similar improvement in the quality of the fits. The magnitude of this Gaussian function was highly correlated with the concentration of β-carotene, with a correlation coefficient of 0.9. Although the quality of the fits is improved with the addition of the Gaussian function, the conclusions regarding the extracted absorber and scattering parameters from the fits are not significantly affected by its addition, and so all subsequent analysis was carried without the inclusion of this Gaussian function.

Figure 6:
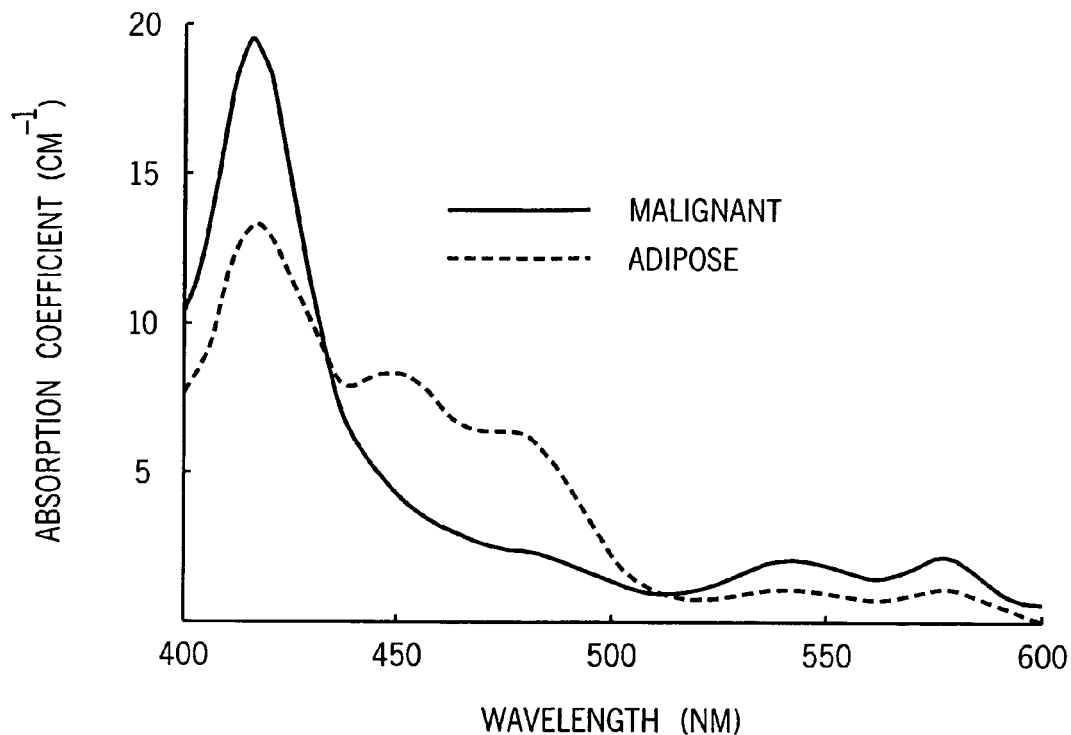
FIG. 6 is a graph of extracted absorption coefficient ($\mu_a$) for the malignant and adipose breast tissues of FIG. 4.
Figure 7:
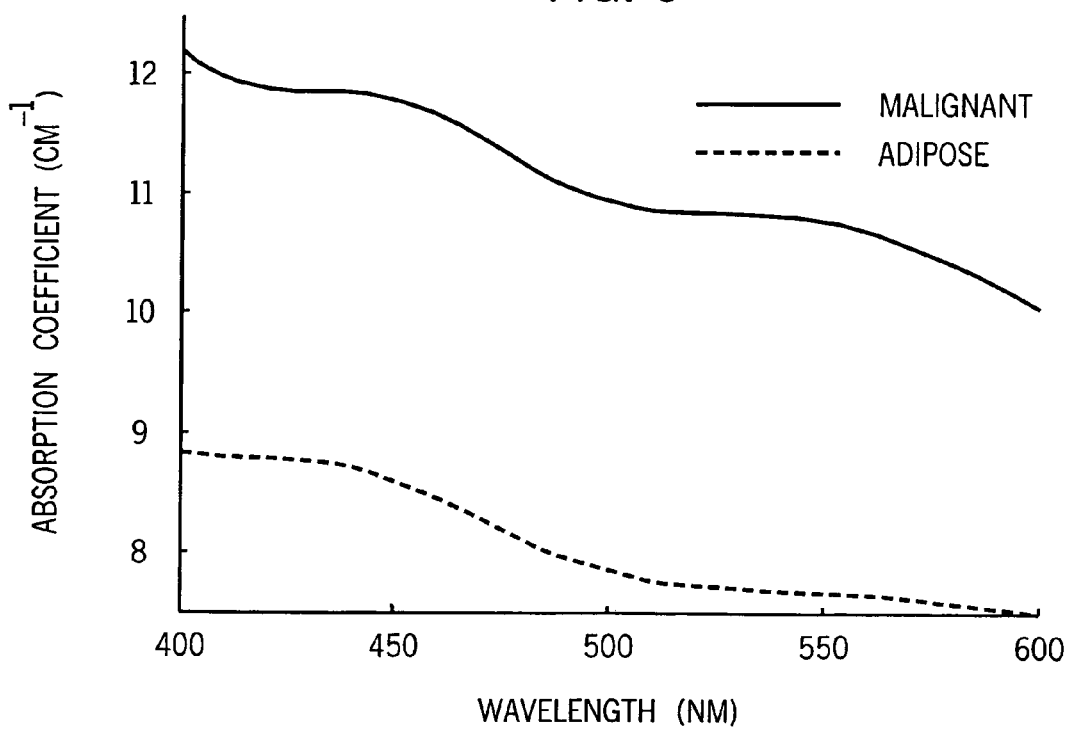
FIG. 7 is a graph of extracted scattering coefficient ($\mu_s$) of the malignant and adipose breast tissues of FIG. 4.

FIG. 6 shows the extracted absorption coefficient $\mu_a$ from the tissues and FIG. 7 shows the reduced scattering coefficient $\mu_s$ spectra extracted from the modeled malignant and adipose tissue diffuse reflectance spectra (obtained without the Gaussian function). It can be seen that both samples have significant hemoglobin absorption, whose peak absorption occurs at approximately 420 nm, and that the malignant sample shows higher hemoglobin absorption compared to that in adipose tissue. Additionally, it can be seen that the adipose tissue sample has a distinctly different line shape in the absorption spectrum, particularly over the wavelength range of 450-500 nm. The absorption in this range is in part due to β-carotene in adipose tissues. It can also be seen that the reduced scattering coefficient $\mu_s$ is substantially reduced in the adipose tissue, compared to that in the malignant tissue.

A Monte Carlo based forward and inverse model has been developed for the extraction of the absorption $\mu_a$ and scattering coefficients $\mu_s$ of turbid media such as human tissue from diffuse reflectance spectroscopy measurements. Upon applying the inverse model to measured human breast tissue diffuse reflectance spectra, three parameters were identified by the Wilcoxon rank-sum test as showing statistically significant differences between the malignant and non-malignant tissue types. These included hemoglobin saturation, β-carotene concentration and the mean reduced scattering coefficient $\mu_s$. A support vector method as described by S. Gunn, "Support Vector Machines for Classification and Regression," University of Southampton: Department of Electronics and Computer Science Website (1998) and as described by C. Burges, "A Tutorial on Support Vector Machines for Pattern Recognition," Data Mining and Knowledge Discovery 2, 121 (1998) using two of the three parameters (hemoglobin saturation and mean reduced scattering coefficient $\mu_s$) yielded a sensitivity and specificity of 82% and 92%, respectively for discriminating between malignant and non-malignant breast tissues.

APPENDIX A

Derivation of Equation 3

Figure 8:
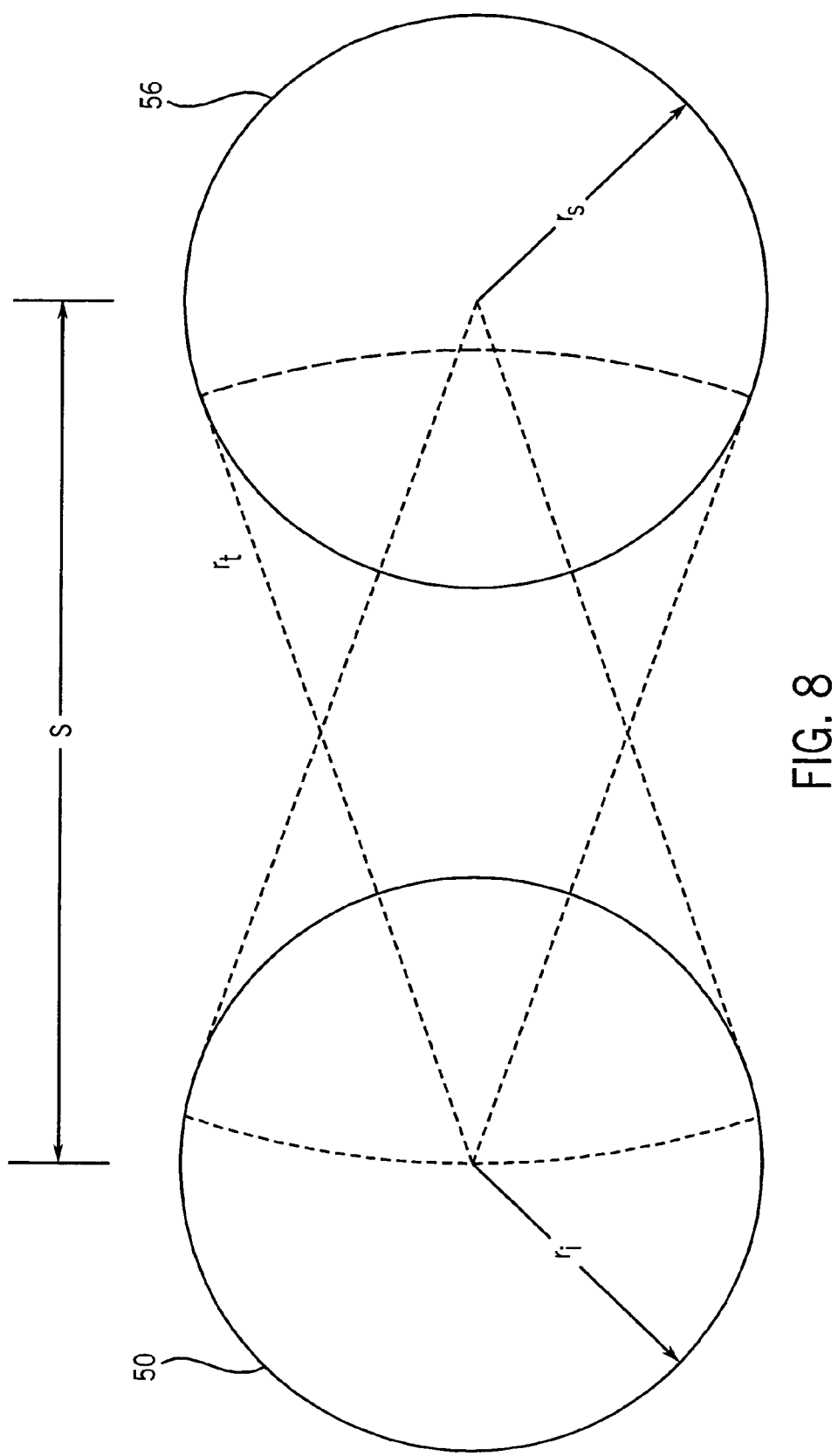
FIG. 8 is a schematic used to explain the derivation of computations made with the preferred method.

Referring particularly to FIG. 8, we wish to derive the probability that a photon launched into a circular illumination fiber or radius $r_i$, which travels a given distance, $r_t$, will be collected by separate circular fiber of radius $r_c$ a fixed center to center distance, s, away. This is derived for uniform fiber illumination and collection efficiencies. Both fibers are normal to the medium, which is a radially and translationally invariant system (such as a homogeneous layered medium).

Let the illumination fiber be centered at the origin, and the collection fiber be centered at (s,0). First we take the case where photons are only launched at the center of the illumination fiber. The photon may exit the surface at the circle centered at the origin, with radius $r_t$. The probability the photon will exit within the region contained by the collection fiber, and thus be collected, is given by $p=r_t\theta/(2\pi r_t)$, which corresponds to the arc length of the exit locations contained within the collection fiber, divided by the total circumference of the circle that defines all possible exit locations. With simple trigonometry, this can be derived to be equivalent to:

$$p = \frac{1}{\pi}\cos^{-1}\left(\frac{r_t^2 + s^2 - r_c^2}{2sr_t}\right), s - r_c < r_t < s + r_c \quad (4)$$

$$p = 0, \text{ otherwise}$$

This can be then be extended to a line source located at y=0, and $-r_i \leq x \leq r_i$ by noting that a displacement in x in the source effectively changes the source detector separation s, and integrating. This is normalized to the length of the source line to produce the average probability for all source locations from which the photon could originate. For the following derivations we will assume the probability of collection is non-zero, i.e. $s-r_i-r_c < r_t < s+r_i+r_c$. In this case the probability of collection is given by:

$$p = \frac{1}{2r_i} \times \frac{1}{\pi}\int_{lb}^{ub}\cos^{-1}\left(\frac{r_t^2 + (s-x)^2 - r_c^2}{2(s-x)r_t}\right)dx \quad (5)$$

Where $ub=\min(r_i, s-r_t+r_c)$ and $lb=\max(-r_i, s-r_t-r_c)$. These bounds correspond to the launch locations for which the probability of collection is non-zero.

Finally, this system can be extended to a fiber source by noting that the probability of collection is the same for any source location at a given distance from the center of the collection fiber. Thus each point in the integral given in equation (5) is weighed by the arc length of all source locations occurring within the source fiber, equidistant to the collection fiber center. The integral is then normalized to the area of the source fiber, to produce the average probability of collection for all possible source locations. This gives:

$$p = \frac{1}{\pi r_i^2} \times \frac{1}{\pi} \quad (6)$$

$$\int_{lb}^{ub}(s-x)\cos^{-1}\left(\frac{s^2+(s-x)^2-r_i^2}{2(s-x)s}\right)\cos^{-1}\left(\frac{r_t^2+(s-x)^2-r_c^2}{2(s-x)r_t}\right)dx$$

With the bounds of the integral being the same as above.

We claim:

1. A method for calculating the scattering and absorption characteristics of tissue, the steps comprising:
   a) acquiring, with an optical spectroscopy system that includes an optical probe having at least one illumination fiber and at least one collection fiber, a set of diffuse reflectance measurements from the tissue;
   b) establishing a set of tissue optical parameters;
   c) calculating model reflectance values using the set of tissue optical parameters and a model which relates diffuse reflectance to tissue optical parameters, and further including:
      i) acquiring information relating to the locations of the at least one illumination and at least one collection fibers within the optical probe; and
      ii) determining a probability that a photon emitted by the at least one illumination fiber is collected by the at least one collection fiber using the information acquired in step c)i);
   d) calculating the sum of squares error between the measured diffuse reflectance and the model reflectance values;
   e) repeatedly updating optical parameters and repeating steps c) and d) until the sum of squares error is substantially minimized;
   f) calculating the scattering and absorption characteristics of the tissue from the updated optical parameters that yield a minimum sum of squares error; and
   wherein step c)ii) includes performing a convolution to integrate between the at least one illumination and at least one collection fiber.

2. The method as recited in claim 1 in which said model is a Monte Carlo model.

3. The method as recited in claim 2 in which the optical parameters include absorber concentration, scatterer size, and scatterer density, and the scattering and absorption characteristics of the tissue includes the scattering coefficient $\mu_s$ of the tissue and the absorption coefficient $\mu_a$ of the tissue.

4. The method as recited in claim 3 which includes calculating the absorption coefficient $\mu_a$ from the absorber concentration using Beer's law.

5. The method as recited in claim 3 which includes calculating the scattering coefficient $\mu_s$ from the scatterer size and scatterer density using Mie's theory.

6. The method as recited in claim 1 which includes:
   g) acquiring a set of diffuse reflectance measurements from a phantom having known optical properties; and
   h) normalizing the set of diffuse measurements of tissue acquired in step a) using the measurements acquired in step g).

7. The method as recited in claim 6 which includes:
   i) normalizing the model reflectance values acquired in step c) using the measurements acquired in step g) prior to performing step d).

8. The method as recited in claim 1 in which one tissue optical parameter is absorber concentration and the method further includes outputting the absorber concentration optical parameter updated in step e).

9. The method as recited in claim 1 in which step c)i) includes acquiring an image of the optical probe to determine the locations of the at least one illumination fiber and at least one collection fiber.

10. A method for calculating the scattering and absorption characteristics of an object, the steps comprising:
    a) acquiring, with an optical spectroscopy system that includes an optical probe having at least one illumination fiber and at least one collection fiber, a set of diffuse reflectance measurements from the object;
    b) establishing a set of object optical parameters;
    c) calculating model reflectance values using the set of object optical parameters and a model which relates diffuse reflectance to object optical parameters, and further including:

i) acquiring information relating to the locations of the at least one illumination and at least one collection fibers within the optical probe; and
ii) determining a probability that a photon emitted by the at least one illumination fiber is collected by the at least one collection fiber using the information acquired in step c)i);
d) calculating the sum of squares error between the measured diffuse reflectance and the model reflectance values;
e) repeatedly updating optical parameters and repeating steps c) and d) until the sum of squares error is substantially minimized;
f) calculating the scattering and absorption characteristics of the object from the updated optical parameters that yield a minimum sum of squares error; and
wherein step c)ii) includes performing a convolution to integrate between the at least one illumination and at least one collection fiber.

11. The method as recited in claim 10 in which said model is a Monte Carlo model.

12. The method as recited in claim 11 in which the optical parameters include absorber concentration, scatterer size, and scatterer density, and the scattering and absorption characteristics of the object includes the scattering coefficient $\mu_s$ of the object and the absorption coefficient $\mu_a$ of the object.

13. The method as recited in claim 12 which includes calculating the absorption coefficient $\mu_a$ from the absorber concentration using Beer's law.

14. The method as recited in claim 12 which includes calculating the scattering coefficient $\mu_s$ from the scatterer size and scatterer density using Mie's theory.

15. The method as recited in claim 10 which includes:
g) acquiring a set of diffuse reflectance measurements from a phantom having known optical properties; and
h) normalizing the set of diffuse measurements of the object acquired in step a) using the measurements acquired in step g).

16. The method as recited in claim 15 which includes:
i) normalizing the model reflectance values acquired in step c) using the measurements acquired in step g) prior to performing step d).

17. The method as recited in claim 10 in which one object optical parameter is absorber concentration and the method further includes outputting the absorber concentration optical parameter updated in step e).

18. The method as recited in claim 10 in which step c)i) includes acquiring an image of the optical probe to determine the locations of the at least one illumination fiber and at least one collection fiber.

* * * * *